US006707254B1

(12) United States Patent
Moisan et al.

(10) Patent No.: US 6,707,254 B1
(45) Date of Patent: Mar. 16, 2004

(54) LOW TEMPERATURE PLASMA STERILISING SYSTEM AND METHOD

(75) Inventors: Michel Moisan, Outremont (CA); Stéphane Moreau, Montréal (CA); Maryam Tabrizian, Longueuil (CA); Jacques Pelletier, Saint Martin d'Héres (FR); Jean Barbeau, Montréal (CA); L'Hocine Yahia, Pointe-Claire (CA)

(73) Assignees: Universite de Montreal, Montreal (CA); Ecole Polytechnique de Montreal, Montreal (CA); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/926,638

(22) PCT Filed: May 26, 2000

(86) PCT No.: PCT/CA00/00623

§ 371 (c)(1), (2), (4) Date: Mar. 19, 2002

(87) PCT Pub. No.: WO00/72889

PCT Pub. Date: Dec. 7, 2000

(30) Foreign Application Priority Data

May 28, 1999 (CA) .......................................... 2273432

(51) Int. Cl.$^7$ ............................ H01J 17/22; A61L 2/00
(52) U.S. Cl. ....................... 315/111.21; 422/22; 422/24
(58) Field of Search ....................... 315/111.21, 111.81, 315/111.91; 422/21, 22, 23, 24; 435/173.1

(56) References Cited

U.S. PATENT DOCUMENTS 4,207,286 A * 6/1980 Gut Boucher ............... 422/21
4,643,876 A 2/1987 Jacobs et al. ................. 422/23
5,213,619 A * 5/1993 Jackson et al. ................ 134/1
5,302,343 A * 4/1994 Jacob .......................... 422/23
5,962,288 A * 10/1999 Aksenov et al. ......... 435/173.1

FOREIGN PATENT DOCUMENTS

WO 92 15336 9/1992
WO 95 26121 9/1995

* cited by examiner

*Primary Examiner*—Don Wong
*Assistant Examiner*—Thuy Vinh Tran
(74) *Attorney, Agent, or Firm*—Oblon, Spivak, McClelland, Maier & Neustadt, P.C.

(57) ABSTRACT

A system and a method for sterilizing objects, in particular medical instruments and accessories, using gas plasma, also called ionized gas. The gases used to form the plasma do not require to exhibit an intrinsic sterilizing activity. The sterilizing properties result from the passage through an electric field generating the plasma, an electric field which is provided by microwaves, a gas stream including oxygen in molecular form ($O_2$) or as a gas element, and atomic or molecular species capable of emitting UV radiation once they have been energized. The system and method provide the advantage of making it possible to treat heat-sensitive and thermolabile objects at temperatures less than 50° C. using gases presenting no risks for the operator.

13 Claims, 4 Drawing Sheets

LOW TEMPERATURE PLASMA STERILISING SYSTEM AND METHOD

TECHNICAL FIELD

The present invention relates to a system and to a process for the sterilization of objects, particularly for the sterilization of medical instruments and accessories, by means of gas plasma, which is also called ionized gas. The gases used to produce this plasma need not have an intrinsic sterilizing ability. The sterilizing properties according to the invention result from the passage of the gas or gases through an electric field creating the plasma, which can be created, for example, by microwaves. The advantage of the invention lies in its ability to treat objects that are heat sensitive and heat labile at temperatures below 50° C. and by using gases, which pose no danger to the operator of the system.

BACKGROUND OF THE INVENTION

Sterilization processes used in hospitals have generated a good deal of controversy lately with the arrival of instruments and accessories made of heat sensitive polymer materials. Presently the autoclave is recognized as an effective means of sterilization, however with the disadvantage of requiring temperatures that are too high (above 121° C.) to permit its use with polymer materials. Furthermore, the longterm use of the autoclave causes irreversible damages to metallic objects and irredeemably modifies some of their physical properties.

To overcome these limitations, sterilization processes using ionized gas, or gas plasma were developed. These processes operate at sufficiently low temperatures to permit the sterilization of instruments and of accessories made of heat sensitive polymer materials. However, few studies have been undertaken to determine the efficiency of these processes relative to their mechanism of destruction of microorganisms.

The use of plasma as a sterilizing agent was initially proposed at the end of the 1960's. U.S. Pat. No. 3,383,163 describes the use of a pulsed electric field for generating an argon or nitrogen plasma, with the goal of sterilizing the internal walls of a flask. The process is such that the sterilization of the flask is directly performed during the discharge.

The interest of such a method increased with the advent of commercial sterilizers such as Sterrad™, produced and sold by Johnson and Johnson, as well as, Plazlyte™, produced and sold by Abtox. However, it is known that with these two types of machines, the plasma does not have a biocidal effect, but merely serves as a detoxification agent that eliminates harmful residues by limiting the oxidizing effects of hydrogen peroxide and of peracetic acid vapors injected as sterilizing agents. It may therefore be considered that those devices use gas plasmas in the sterilization process, but with the distinction that the aforementioned sterilization is achieved by the addition of chemical species and not through the action of activated plasma species.

Therefore, it would be advantageous to develop a total sterilization system and process, that employs only a low cost gas and without any risk to the operator. The gas or mixture of gases could be activated at low temperature by a plasma, then applied on the object that is to be sterilized, thereby generating biocidal species that allow for the sterilization of said object, no matter what material the object is made of.

IN THE DRAWINGS

Figure 7:
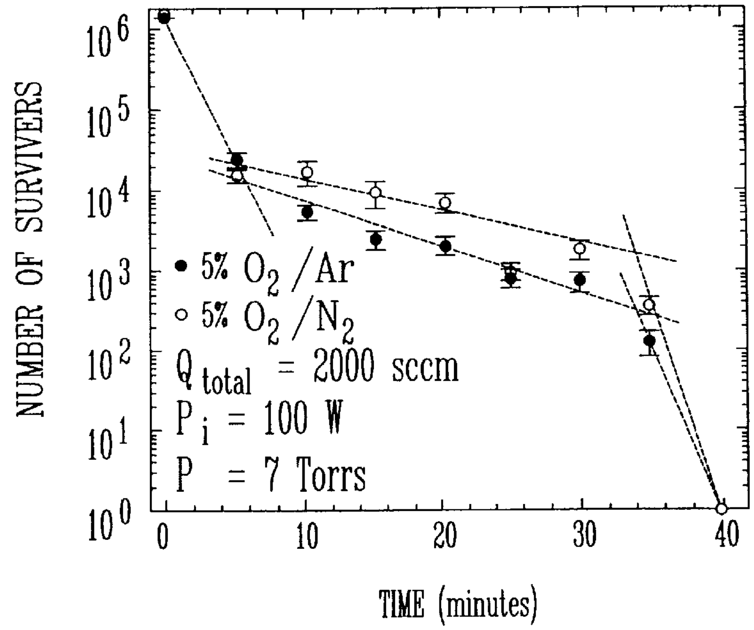

FIG. 7 compares the rate of survival of spores in the sterilization treatment process of the present invention as a function of time in post-discharge by using a 5% $O_2$/95% Ar or by using a 5% $O_2$/95% $N_2$ mixture in the discharge tube.

SUMMARY OF THE INVENTION

The present invention relates to a process for the sterilization of objects, which comprises exposing the objects to a plasma containing sterilizing species generated in situ when a gaseous flux comprising between 0.5% and 20% of atomic oxygen, is exposed to an electric field of an intensity sufficient to generate a plasma. The sterilizing species generated will destroy microorganisms, even though the gas has no biocidal properties prior to its passage through the electric field. In a preferred embodiment, the objects to be sterilized are exposed outside the zone of plasma excitation also known as the post-discharge zone.

In another aspect of the invention, there is provided a means of sterilization comprising a plasma source coupled to a sterilization chamber by means of a discharge tube into which a gas or a mixture of gases, which eventually generates the plasma, is injected. The chamber contains an object to be sterilized and is connected to a vacuum pump that carries the gases into the chamber and maintains therein a reduced pressure. Preferably, the plasma source consists of an electric field such as a surfatron or a surfaguide.

DETAILED DESCRIPTION OF THE PREFERRED EMBODIMENT

The present invention concerns a system and a process using as gas flux, a plasma, that forms atomic and molecular species having a biocidal action. These species generated in situ permit the sterilization of objects at temperatures below 50° C. and without danger to the operator. The gases used according to the invention, present no danger to the operator or the patient, even if the aeration period after sterilization is insufficiently long. As a matter of fact, the invention may use gases that convert to atomic, free radical, molecular, and photon species having biocidal action only after having been submitted to the action of an electric field. This electric field may result, for example, from a source of continuous or radio frequency current, or from microwaves, these fields being constant or pulsating. The process of the invention can be used in an isolated or repetitive manner, for example in a sequence of several process steps. Possible examples of such process steps may consist of: a gas pulsed in a continuous electric field; a pulsating field in a continuous gas flow; a gas pulsed in a pulsating field in a synchronized manner; a change of gas; or a combination of these steps.

The sterilization is preferably performed in post-discharge, in a gaseous flow of various gases or mixtures of gases. The possible gases include but are not limited to: nitrogen, neon, argon, krypton, xenon, helium, oxygen, carbon monoxide; carbon dioxide, Nox gases; air and mixtures thereof; oxygen may on the other hand be found in various molecular forms that include, $O_2$, $O_3$ or as an element of another gas (e.g. $H_2O$, CO, $CO_2$ etc.). Due to their low level of toxicity, argon, nitrogen and molecular oxygen $O_2$ represent the preferred gases. More harmful gases such as NOx and CO should ideally, only be present at low concentrations to minimize the health risk to the operator and/or to patients.

It was also found that the presence of molecular oxygen ($O_2$) in the gas mixture, in well defined proportions would permit, when in combination with UV rays, a synergy such that the exposure period of the object, in the post-discharge zone or not, is significantly reduced. More specifically, the concentration of molecular oxygen should be between 0.5 and 20%. The percentage of oxygen in a given gas flow is adjusted as a function of the optimization of UV radiation, where the intensity of radiation acts directly on the total time necessary for a complete sterilization. In other words, the percentage of oxygen in the gas flow is adjusted to obtain a maximum UV radiation thus reducing the minimum sterilization time. This adjustment can easily be achieved by any trained person versed in the technique, by using emission spectroscopy to register UV emission (titration method described below) or any other methods (of titration) allowing to obtain similar results. Experimental results obtained show that below 0.5% and above 20%, there is no significant synergy observed. A mixture of 2% O2/98% N2 represents a particularly advantageous operating mode.

In comparison to a treatment in an autoclave, the present process allows a complete sterilization at temperatures that do not exceed 50° C. and at a reduced pressure (in the order of 1 Torr) instead of 121° C. minimum and of a pressure greater than 1 atmosphere, which is required in an autoclave. This means that most objects made in part or in whole of polymer materials, such as, "hand-pieces" of dentists or catheters, can be sterilized without losing their initial properties by the process of our invention.

It is now important to define the term "plasma" as understood according to the present invention. Plasma includes ions and electrons, free to move which are produced by submitting a neutral gas to a sufficiently intense electric field to accelerate the charged particles, which then by exchanging their energy during collisions ensure the maintenance of the plasma state. At times, a distinction is established between a plasma and an ionized gas, due to the fact that a plasma is generally very hot and only contains charged species, while ionized gas is cooler and includes in addition to charged particles, non-charged particles in the form of atoms, radicals or molecules. Although the present invention deals primarily with ionized gases, the common term used in the field of activity of the invention is "plasma" and this term will be used in the present description.

The field of application targeted by this invention is the sterilization of all types of objects, manufactured of any kind of material. Generally, instruments and accessories found in hospitals are manufactured of metal, ceramic and/or polymers. The present invention particularly enables to remedy certain deficiencies and limitation of the current systems i.e.:

it is possible to sterilize an object without exposing it to temperatures above 50° C., which appears to be an essential characteristic, for example, for objects produced in whole or in part of a thermal sensitive material such as a polymeric material;

the sterilizing action of the process comes from atoms, radicals, and photons generated in situ, that is to say initially produced in the electric discharge, or from a subsequent interaction in the said zone of post-discharge, and in both cases, from gases which in themselves have no sterilizing activity or action. The gases or mixtures of gases selected for this use must not endanger the operator, in case the gas comes into contact with the effluents of treatment or with the objects to be treated, during or immediately after sterilization.

The present invention can also be used for the sterilization of objects contaminated with microorganisms, such as molds and microscopic fungi, which are, for example found in ancient books.

The particles, neutral or charged, inside the plasma can be in an excited state, compared to their steady state, therefore containing an internal energy. This internal energy can be spontaneously liberated by emitting a photon, or also through collisions with other particles or with a surface, such as the surface of the microorganisms to be inactivated. The process of collisions can lead to a heating of this surface or to chemical reactions with it, such as oxidation, leading to the formation of a volatile compound linking this radical (atom or molecule) which is present on the surface, and an atom of the surface. Photons from the UV range are particularly effective for this purpose, due to their high internal energy that allows them to break a large number of chemical bonds. The various species generated by an electric discharge are therefore able to damage cellular material (eg. Proteins, DNA, enzymes etc.) and thus exert a biocidal effect.

The process of the present invention allows the destruction of micro-organisms such as bacteria, spores, viruses, mushrooms and prions (non-conventionally transmissible agents) in a short space of time, by the action of an electric field in such a way that the gas to which they are exposed, generates atoms, radicals and molecules whose combined physico-chemical action, as emitted particles or photons generated by the particles, causes the cellular death of these germs. Of course, the process of the invention does not prevent the use of a gas having intrinsic sterilizing properties, alone or in combination with gases having no sterilizing properties.

The sterilization by plasma according to the present invention can be carried out inside the electrical discharge with direct exposure to the plasma, or outside of it. In the latter case, benefit is drawn from species transported by the flow of gas from the discharge to the area called the post-discharge. The post-discharge includes few charged species as compared to the discharge itself, but has almost the same number of active neutral species as the discharge itself. The use of sterilization in the area of post-discharge represents a particularly preferred embodiment for three reasons:

when the created plasma is of high density, for example, with microwaves of 2.45 GHz, the gas temperature of the post-discharge is lower than that at the discharge itself, which substantially lowers the risk of damage to the sterilized objects;

because there are fewer charged particles in the post-discharge, exposed surfaces are less or not at all exposed to an ionic bombardment; and the post-discharge permits, for a comparable price, the use of a larger treatment volume than with the discharge alone.

During a direct discharge exposure, a relatively low treatment temperature can be obtained by using a discharge from direct current (DC), which means a constant electrical field, or by using radio-frequency(RF) discharges, respectively in conditions of low current and of low power RF, or by maintaining a pulsed discharge.

Of course, in order to realize an effective sterilization in the post-discharge, the operator must ensure beforehand that sufficient reactive or "sterilizing" species are found in the zone.

Reactions may also take place in the post-discharge, which produce new species. Some of these neutral species can be in their excited state and can occasionally emit a photon during their trip through the chamber of post-reaction.

In another mode of operation of the invention, it is possible to introduce one or more gases in the discharge and optionally to add, even in the post-discharge, one or more gases. This embodiment is particularly interesting when gases such a $CF_4$ or $SF_6$ are used where the decomposition in the electrical discharge would involve substantial wear of the discharge tube. These different possibilities allow, if necessary, to maximize the sterilizing action of the device while minimizing the long term damaging effects of treatment on objects to be repetitively sterilized.

This technique can be used in an isolated manner or repetitively in multiple step sequential processes, e.g., pumping cycle followed by a gas plasma feed. The choice of the type of discharge to feed the post-discharge depends on the type of radicals wanted. Thus, in order to maximize atomic nitrogen concentration for a given dissipated power in the discharge, one will use a microwave discharge (≧300 MHz). In order to minimize the cost of such a device, the frequency of microwave ovens, that is 2.45 GHz, may be selected. Alternatively, direct exposure to the plasma can be used provided that frequencies in the range of radio frequencies (in the order of 100 MHz) would be used since the plasma density is typically lower in this case.

Figure 1:
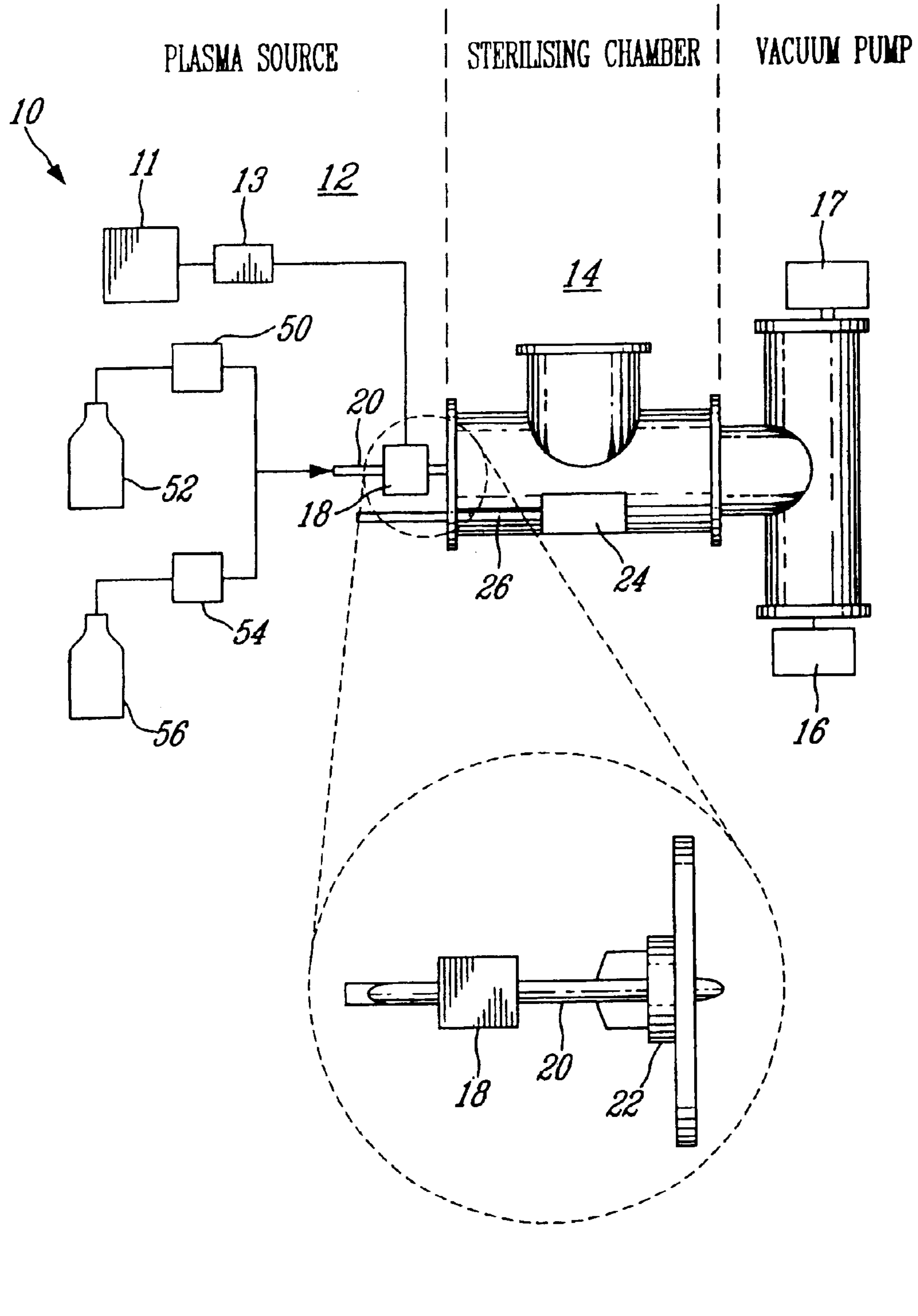
FIG. 1 illustrates a system of sterilization according to the present invention where treatment occurs in post-discharge.
Figure 2:
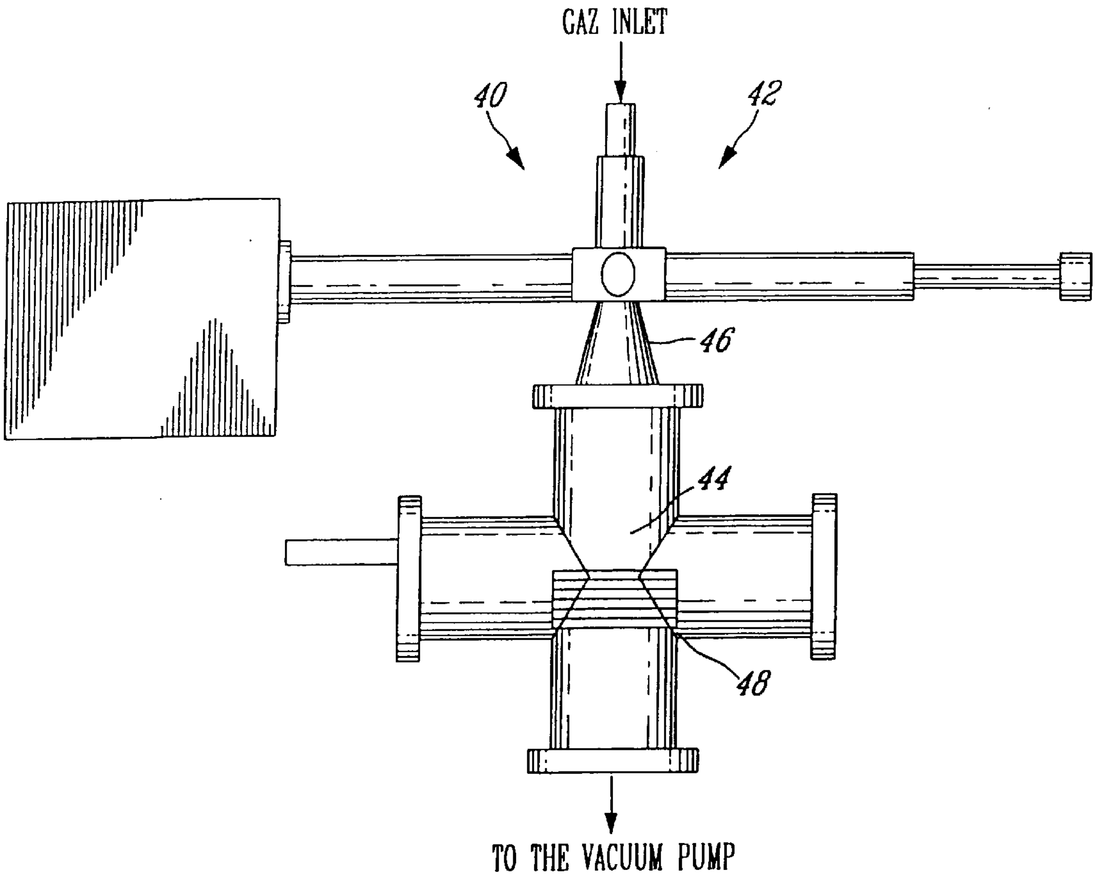
FIG. 2 illustrates a second sterilization system according to the present invention.

By referring to the features which illustrate the preferred embodiments of the present invention, without limiting its scope, a device for sterilization 10 comprising a plasma source 12, a $N_2$ mass flow controller 50, a $N_2$ source 52, an $O_2$ mass flow controller 54, an $O_2$ source 56 a post-discharge or sterilization chamber 14, a vacuum pump 16, and a pressure indicator 17 which controls the gas rate, may be found on FIG. 1. The plasma is produced by a microwave discharge at 2.45 GHz by propagation of an electromagnetic surface wave at a maximal power of 180 W from a generator 11. The power is measured from a counter 13. For a power of about 100 W or more, it is preferable, particularly if the object to be sterilized is thermally sensitive, to cool the discharge tube 20 with compressed air. The surface wave is excited by a conventional surfatron 18. Any other device for exciting the surface wave, such as those described in U.S. Pat. Nos. 4,043,940; 4,810,933 or in *J. Phys. D.: Appl. Phys.* 1991, 24, 1025–1048 may be used, which allows the broadening of the range of possible frequencies from a few MHz to some GHz. The diameter of the discharge tube 20 through which the plasma is injected in chamber 14 is not critical, but is preferably chosen in order to optimize the production of requested species for the sterilization. According to the embodiment illustrated in FIG. 1, the internal diameter of the tube is of 8 mm and its length is 300 mm. Any person skilled in the art would be able to determine easily the suitable diameter for a proposed application. The discharge tube may be fabricated with any material compatible with the operation of the system, for example from molten silica.

In order to prevent overheating of sealing elements (o-rings) placed between chamber 14 and tube 20, which is generated by the microwaves and the plasma, the diameter of tube 20 is expanded to 30 mm at extremity 22 which is adjacent to chamber 14. The gas(es) is (are) introduced into tube 20 at a rate which is adjusted with the help of a flowmeter (for example, 50 and/or 54) which is previously calibrated. The gases are conducted into chamber 14 by means of pump 16 generating a primary vacuum (residual vacuum of 30 to 50 mTorr). A more or less important throttling of the pump allows the gas pressure to be fixed in the reactor. Evacuation of the gas from pump 16 is done outside the building, eventually through appropriate filters. The pressure inside the chamber is preferably reduced at a value situated between 30 and 50 mTorr, and the pressure of the gas entering the chamber is adjusted preferably between 1 and 7 Torr.

Chamber 14 has a volume of 20 liters, and is made of Pyrex™ (i.e., borosilicate glass), but can be made of any material compatible with the reaction mixture. Pyrex™, due to its transparency, is particularly advantageous since it allows observations by emission spectroscopy, to see the effects of the positioning of the object to be sterilized on the gaseous flux, etc. Advantageously, the objects to be sterilized are placed in a support 24 that is preferably made of stainless steel. The form of the support is suited to facilitate its cleaning after use, as well as the retrieval of the sterilized objects. In order to check the temperature in the support 24, it is possible to circulate in it, in a closed circuit, a cooling liquid inside a duct 26, also made of stainless steel.

In another embodiment of the invention, a second device for sterilization 40 has also been tested. The latter comprises a plasma source 42 comprising a surfaguide, a post-discharge or sterilization chamber 44 and a vacuum pump (not illustrated). The plasma is again produced by a microwave discharge at 2.45 GHz by propagation of an electromagnetic surface wave at a maximal power of 180 W that is transmitted by the surfaguide. The surface wave is excited by the surfaguide. The discharge tube 46 has an internal diameter of 40 mm. Chamber 44, in which is placed support 48, is made of stainless steel. The other features of this device are relatively similar to those of the device illustrated in FIG. 1. It is however interesting to note that in this embodiment, the gaseous flux comes into contact perpendicularly to the object to be sterilized while according to the device of FIG. 1, the contact is made in parallel.

Other forms of plasma sources as well as other configurations and dimensions of the sterilization chamber could be advantageously used according to the process of the invention. Thus, the sterilization chamber could be equipped with an entry door for the introduction and the removal of the objects to be sterilized. The same remark applies to the support that could take forms more suited for the pieces to be sterilized.

The present system has been tested by sterilizing crucibles contaminated with reference spores conventionally used for the efficiency control of commercial sterilizers, such as *Bacillus subtilis* var. Niger (ATCC 9372) and *Bacillus stearothermophilus* (ATCC 7953). The initial population of spores is about $10^6$ individuals.

According to the process of our invention, once the post-discharge chamber is evacuated, the duration of a complete sterilization cycle is about 40 minutes and the objects to be sterilized are available about 5 minutes later, this is the time necessary to bring the reactor back to atmospheric pressure. By comparison, processes with ethylene oxide need a few hours of ventilation after the sterilization cycle, since there is a danger for the operator and for the patient. The process of the present invention allows a time gap that is considerable by comparison to the method using ethylene oxide. Moreover, the gases used for the present process have no toxic or noxious effects on the operators and/or the patients, in a room which is normally ventilated. The duration of the treatment according to the present invention may be reduced by increasing the concentration of "sterilizing" species inside the sterilization chamber, for example by adding one or more sources of plasma, or also by optimizing the composition of the gaseous mixture, or if necessary any other experimental parameter such as temperature, gas flow rate, pressure inside the chamber, etc.

Figure 3:
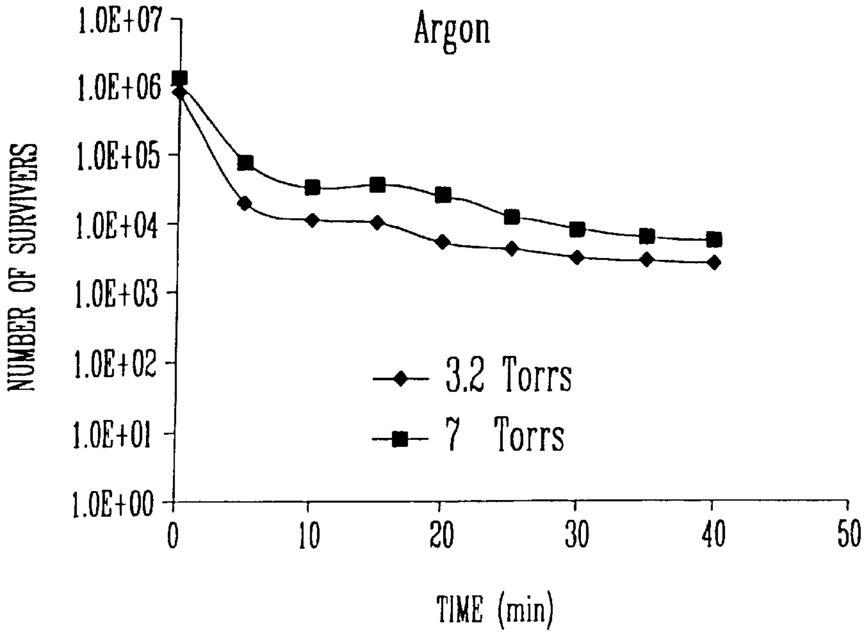
FIG. 3 illustrates the number of spores that survived a sterilization treatment process involving the present invention as a function of time in post-discharge using pure argon in the discharge tube.

FIG. 3 shows the results obtained, in post-discharge, with the device of FIG. 1, by simply using pure argon, introduced into the discharge tube, at two different pressures into the reactor, at a speed of 2 liters/minute under standard conditions with a 100 W power. As may be seen, the sterilization is far from complete. For this figure, each point on the graphic represents the average value obtained for 5 trials realized under similar conditions. Comparable results are obtained by replacing argon with nitrogen.

Figure 4:
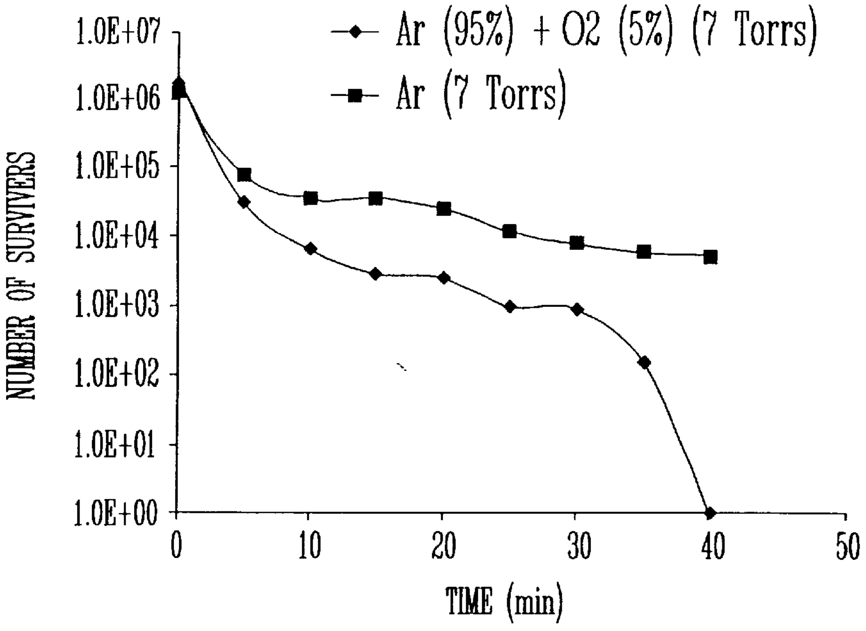
FIG. 4 illustrates the number of spores that survived a sterilization treatment process of the present invention as a function of time in post-discharge using pure argon or a 5% $O_2$/95% Ar mixture in the discharge tube, wherein the gas is introduced in both cases by the discharge tube.

FIG. 4 shows the results obtained, in post-discharge, with the device according to FIG. 1 by using pure argon, or a mixture 5% $O_2$/95% Ar. In both cases, the introduction of gas(es) is made through the discharge tube, at a rate of 2 liters/minute. The presence of oxygen in the mixture ensures a complete sterilization in 40 minutes. For this figure as well as for the following ones, each point on the graphic represents the average value obtained for 6 trials realized under similar experimental conditions.

Figure 5:
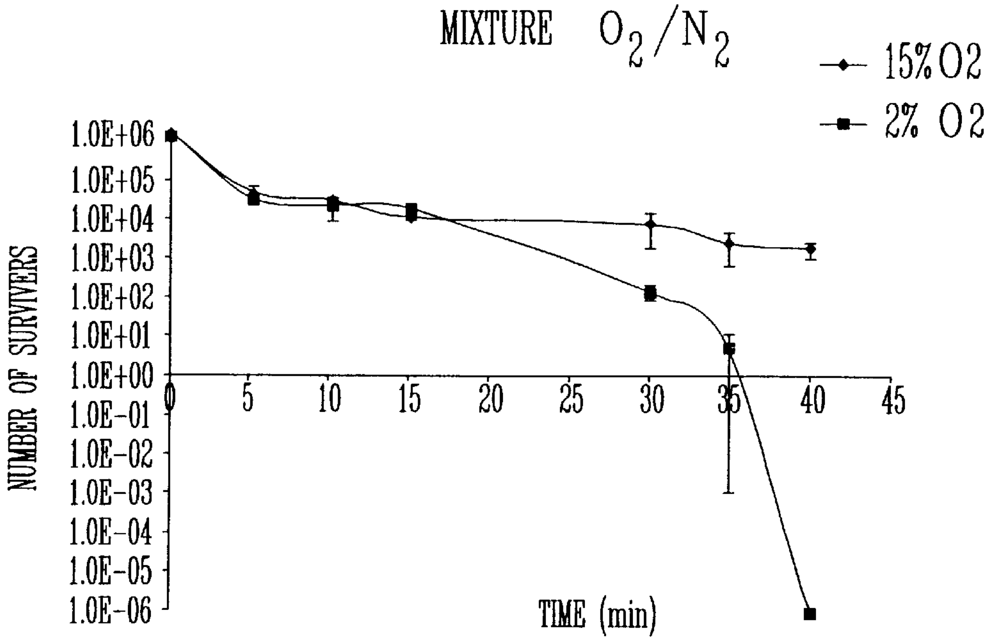
FIG. 5 illustrates the survival rate of spores in the sterilization treatment process of the present invention as a function of time in post-discharge using a 15% $O_2$/85% $N_2$ (maximum concentration of atomic oxygen) or using a 2% $O_2$/98% $N_2$ (maximum UV radiation NO) mixture in the discharge tube.

FIG. 5 illustrates the results obtained which two mixtures $O_2/N_2$. In the first case, the oxygen concentration has been optimized in order to optimized the molecular oxygen (15% $O_2$/85% $N_2$), wherein in the second case (2% $O_2$/98% $N_2$), the most important intensity possible for the UV radiation coming from the NO molecule (320–280 nm), was sought. In order to determine the percentage of $O_2$ resulting in the maximum concentration of molecular oxygen, a conventional titration method such as the one described in *Plasma Sources Science and Technology*, 1998, 7, 550–556 has been used. In order to determine the maximum of $O_2$ leading to a maximum UV intensity, a spectroscopic recording has been realized in a wavelength range of about 320 nm. In both cases, the pressure in the reactor was of 2.3 Torr and the flowrate of gas was 500 mL/min under standard conditions. The results of FIG. 5 clearly establish that the presence of UV plays a crucial role in achieving a complete sterilization and in a relatively short time, and that a synergistic effect exists between oxygen and UV radiation. The results illustrated on FIGS. 4 and 5 show that the achieving of complete sterilization varies according to the gaseous mixture used, but also according to the proportion of each gas present in the mixture itself.

Figure 6:
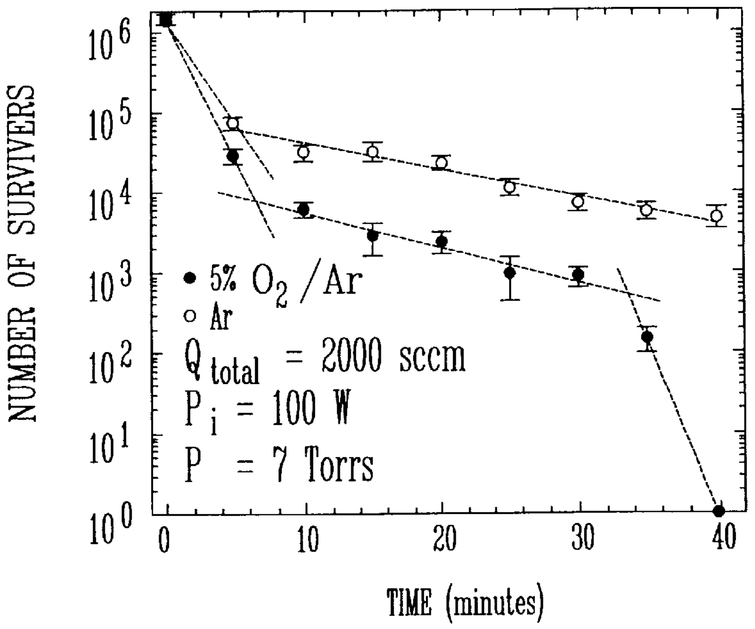
FIG. 6 illustrates the survival rate of spores in the sterilization treatment process of the present invention as a function of time in post-discharge, using a 5% $O_2$/95% Ar mixture in the discharge tube.

It is well known that the presence of oxygen in the discharge increases the inactivation of spores by plasma. Therefore, FIG. 6 illustrates a mixture 5% $O_2$/argon, which confirms the role of oxygen. The point appearing at $10^0$ corresponds to the absence of spore detection, i.e., it is therefore possible to consider the sample sterile.

FIG. 7 compares the number of surviving spores after the utilization of 5% $O_2$/95% Ar and 5% $O_2$/95% $N_2$ mixtures at the same pressures and flow rates. In each case, the sample appears to be sterile after about 40 minutes. Nitrogen, due to its cost, which is significantly cheaper than argon, may therefore be preferred.

The flow of gas in the sterilization chamber may vary according to the pressure inside said chamber, but in order to obtain an optimal performance for the sterilization, it has been found that preferential conditions for the operation of the process according to the invention require a gas flow rate ranging from 0.5 to 2 liters per minute, with a pressure of about 1 to 10 Torr. Moreover, by bringing the object to be sterilized up to a certain temperature, which is fixed, for example at 50° C., by infrared radiation or by other means, appears to activate the destruction of the spores.

The use of low temperature plasmas, typically lower than 50° C., without the addition of a very active, and therefore unstable, chemical entities, represents therefore a reliable and efficient alternative for the sterilization of thermally sensitive objects, such as those fabricated with polymeric materials such as endoscopes or catheters.

Even though the present invention has been described with reference to specific embodiments, it is clear that many variations and modifications may be added to those embodiments, and the present application intends to cover such modifications, uses or adaptations of the present invention according, in general, to the principles of the invention and including any variation of the present description which will become known or conventional in the field of activity of the present invention, which may apply to the above-mentioned essential elements, in accordance with the scope of the following claims.

The embodiment(s) of the invention described above is(are) intended to be exemplary only. The scope of the invention is therefore intended to be limited solely by the scope of the appended claims.

What is claimed is:

1. A process for sterilization of objects, which comprises exposing said objects to a plasma comprising sterilizing species generated in situ, by subjecting a gaseous flow comprising between 0.5% and 20% of molecular oxygen, to an electric field which is sufficiently intense to generate said plasma, allowing the sterilizing species to destroy microorganisms and prions, said gaseous flow used having no biocidal property prior to passage thereof through the electric field, wherein in said process:

the percentage of molecular oxygen present in the gaseous flow is adjusted in such a manner to give a maximal UV (ultraviolet) radiation; and the step of exposing is carried out in a post-discharge zone or in a zone of excitation of the plasma.

2. The process according to claim 1, wherein the electric field is generated by a microwave discharge.

3. The process according to claim 1, wherein the sterilizing species comprise at least one of photons, free radicals, and molecules.

4. The process according to claim 1, wherein the gaseous flow comprises, in addition to molecular oxygen, nitrogen, neon, argon, krypton, xenon, helium, oxygen, carbon monoxide, NOx with x representing a whole number selected from the group consisting of 1, 2, or 3, carbon dioxide, air, and their mixtures thereof.

5. The process according to claim 1, wherein said gaseous flow includes in addition to molecular oxygen, nitrogen, argon, and mixtures thereof.

6. The process according to claim 1, wherein a proportion of oxygen in the gaseous flow varies between 2% and 5%.

7. The process according to claim 1, wherein the microorganisms include viruses, spores, bacteria, fungi, and molds.

8. The process according to claim 1, wherein the process is carried out at a temperature of 50° C. or less.

9. The process according to claim 1, wherein the process is carried out in an isolated manner or in a repetitive multi-step sequential process.

10. The process according to claim 9, wherein the steps include a gas pulsated in a continuous electric field, a field pulsated in a continuous gas flow, a gas pulsated in field pulsated in a synchronous way, a change of gas, or a combination of these steps.

11. A device allowing the operation of the sterilization process according to claim 1, comprising a plasma source coupled to a sterilization chamber by a discharge tube, wherein a gas or a gas mixture which eventually generates the plasma is injected, said chamber containing an object to be sterilized, a vacuum pump for carrying the gases into the chamber and for maintaining a reduced pressure, and a massflow controller for oxygen adjustment, wherein in said device the plasma source comprises a surfatron or surfaguide electric applicator.

12. The device according to claim 11, wherein the sterilization chamber is constructed entirely or partially of borosilicate glass.

13. The device according to claim 11, wherein the sterilization chamber includes a support for the object to be sterilized.

* * * * *

UNITED STATES PATENT AND TRADEMARK OFFICE

CERTIFICATE OF CORRECTION

PATENT NO. : 6,707,254 B1
DATED : March 16, 2004
INVENTOR(S) : Moisan et al.

It is certified that error appears in the above-identified patent and that said Letters Patent is hereby corrected as shown below:

Title page,
Item [75], Inventors, should read:
-- [75] Inventors: Michel Moisan, Outremont (CA);
Stéphane Moreau, Montréal (CA);
Maryam Tabrizian, Longueuil (CA);
Jacques Pelletier, Saint Martin d'Héres (FR) --.

Signed and Sealed this

Sixth Day of September, 2005

JON W. DUDAS
*Director of the United States Patent and Trademark Office*